United States Patent [19]
Wise

[11] Patent Number: 4,983,331
[45] Date of Patent: Jan. 8, 1991

[54] METHOD FOR FORMING A PATTERN FOR PRODUCING OCCLUSAL SPLINTS

[76] Inventor: Thomas B. Wise, 2568 Cheyenne Pl., Saginaw, Mich. 48603

[21] Appl. No.: 388,119

[22] Filed: Aug. 1, 1989

Related U.S. Application Data

[62] Division of Ser. No. 197,516, May 22, 1988, Pat. No. 4,881,713.

[51] Int. Cl.$^5$ .............................................. A61C 13/00
[52] U.S. Cl. ...................................... 264/16; 264/220; 264/294
[58] Field of Search ................. 264/16, 299, 320, 322, 264/294, 325, 220; 433/6; 249/54; 128/861, 862

[56] References Cited

U.S. PATENT DOCUMENTS

| | | | |
|---|---|---|---|
| 4,044,762 | 8/1977 | Jacobs | 128/136 |
| 4,114,614 | 9/1978 | Kesling | 128/136 |
| 4,365,783 | 12/1982 | Kesling | 249/124 |
| 4,419,992 | 12/1983 | Chorbajian | 128/136 |
| 4,672,959 | 6/1987 | May et al. | 128/136 |

Primary Examiner—Jan H. Silbaugh
Assistant Examiner—Christopher A. Fiorilla
Attorney, Agent, or Firm—Learman & McCulloch

[57] ABSTRACT

A preformed pattern for forming an occlusal splint having a U-shaped member composed of material that is form-stable at room temperature and sufficiently pliable at an elevated temperature to be conformed to the bits of a person's jaw or to a model of such person's jaw.

6 Claims, 1 Drawing Sheet

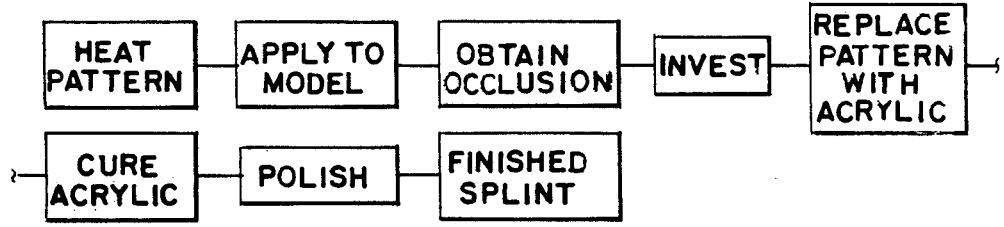
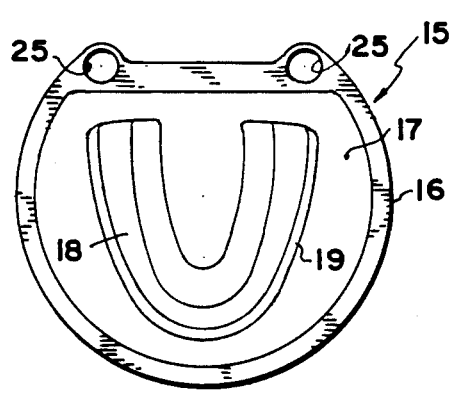
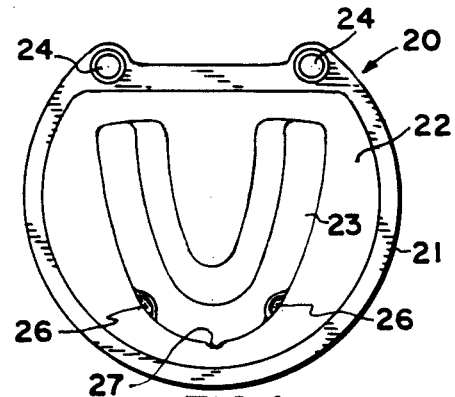
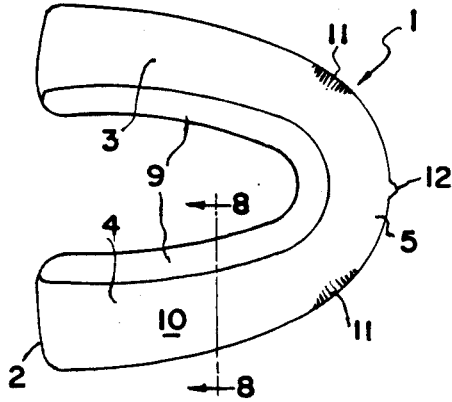
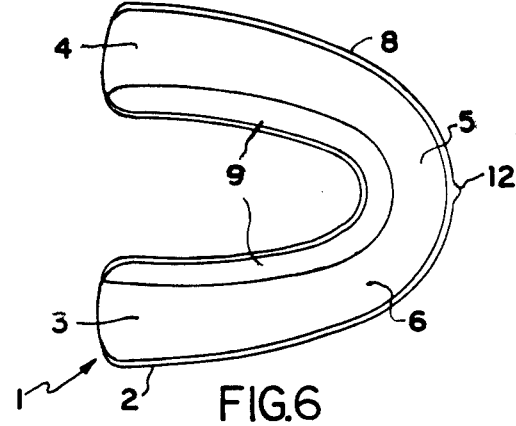
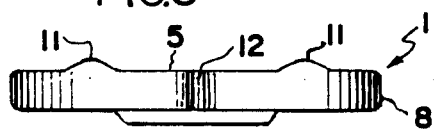
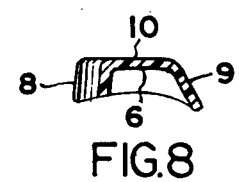

METHOD FOR FORMING A PATTERN FOR PRODUCING OCCLUSAL SPLINTS

This is a divisional of copending application Ser. No. 07/197,516 filed on May 22, 1988, now U.S. Pat. No. 4,881,713.

This invention relates to a preformed pattern for use in the production of dental splints and to methods of forming such patterns.

BACKGROUND OF THE INVENTION

It is known to use occlusal splints for combatting bruxism and periodontal problems, to relieve strain on the temporal mandibular joint, and for other well-known purposes. The use of patterns in the manufacture of such splints is common and millions of such patterns are used every year. Heretofore, however, the production of such patterns has been a tedious, manual operation requiring the services of a dental professional or a highly skilled dental technician.

In general, one procedure currently in use for the production of a splint pattern involves the formation of plaster models of a patient's maxillary and mandibular jaw teeth, placing the models in an articulator, heating a quantity of dental wax to make it manually pliable, and thereafter shaping the pliable wax to form an arcuate approximation of the patient's bite. While still pliable the arcuate member is inserted between the maxillary and mandibular jaw teeth models and conformed as much as possible to the configuration of the patient's teeth, following which an impression is made of the patient's bite in the still pliable arcuate member so as to form a pattern which subsequently may be used in the production of the splint.

Another current method for forming a splint pattern corresponds substantially to that described above except that the pattern is formed directly in the patient's mouth without the use of models or an articulator.

The manner of forming patterns as described above has many disadvantages other than the time expended in the production. For example, the labial and buccal length and wall thickness rarely, if ever, are uniform. In addition, those patterns which are used for the production of splints having cuspid risers must have excess wax applied manually, a procedure which leaves a great deal to be desired in terms of location, thickness, height, and slope. Further, the manual formation of a splint pattern from maxillary and mandibular models presents problems in effecting precise orientation of the pattern in the patient's mouth.

A splint pattern formed in accordance with the present invention overcomes or greatly minimizes all of the foregoing objections.

SUMMARY OF THE INVENTION

A pattern formed in accordance with the invention comprises a substantially U-shaped member having spaced apart limbs converging in a direction toward one end of such member and being joined at corresponding ends by an arcuate bight. The member has a relatively flat base from one surface of which spaced apart inner and outer side walls extend in the same direction. The opposite surface of the base is relatively flat except for a pair of upstanding protrusions spaced from one another along the arc of the bight. Each protrusion has its maximum height substantially in the plane of the adjacent side wall and declines smoothly and substantially uniformly toward the otherwise flat surface. If the splint is adapted to be applied to the maxillary jaw, the protrusions are located at the labial or outer side wall, whereas if the splint is adapted to be fitted to the mandibular jaw, the protrusions are located at the lingual or inner side wall. At the midpoint of the bight the labial side wall is provided with a forwardly extending ridge or projection which preferably extends the full height of the wall.

The protrusions provided on the otherwise flat surface of the pattern are for the purpose of enabling the finished splint to have cuspid risers at the proper locations. The forwardly projecting ridge is provided to facilitate proper orientation of the pattern in the molded articulator or the patient's mouth.

The pattern is formed by a molding process wherein dental wax or other suitable material, form-stable at room temperature and flowable at elevated temperatures, is placed in a mold and subjected to sufficient pressure to enable the base and side walls of the pattern to be formed to the proper configuration and wall thickness. The molded part is removed from the mold and trimmed to form the pattern. The pattern will have the cuspid risers and the locating ridge as integral parts thereof. Patterns thus formed then may be delivered to dentists and/or dental technicians who will be able to use them in the conventional manner for the production of dental splints.

THE DRAWINGS

Methods and apparatus according to the invention are disclosed in the following description and in the accompanying drawings, wherein:

FIG. 1 is a flow chart illustrating the steps involved in the production of a finished pattern;

FIG. 2 is a flow chart illustrating the steps involved in making a finished splint from a pattern;

FIG. 3 is a top plan view of one half of a mold for making a pattern;

FIG. 4 is a bottom plan view of the other half of the mold;

FIG. 5 is a top plan view of the finished pattern;

FIG. 6 is a bottom plan view of the pattern;

FIG. 7 is a front elevational view of the pattern; and

FIG. 8 is a sectional view taken on the line 8—8 of FIG. 5.

DETAILED DESCRIPTION

A splint pattern constructed in accordance with the invention is designated generally by the reference character 1 in FIGS. 6–8 and comprises a generally U-shaped member 2 having spaced apart limbs 3 and 4 converging in a direction toward one end of the member and being joined at corresponding ends by an arcuate bight 5. The member 2 has a base 6 from the inner surface of which spaced apart, upstanding side walls 8 and 9 extend in the same direction.

The opposite, outer surface 10 of the base 6 is substantially flat and smooth except for a pair of protrusions 11 spaced along the arc of the bight 5. In the disclosed embodiment, the protrusions 11 are located at positions corresponding to those of a person's cuspids and each protrusion has its point of maximum height substantially coplanar or flush with the adjacent outer wall 8 and slopes or declines uniformly from such point toward the surface 10. The maximum height of each protrusion above the surface 10 is between about 2 and 3 mm.

At the midpoint of the bight 5 is a protruding ridge 12 which preferably extends the full height of the outer wall and has a height of between about 1 and 1.5 mm. The width of the ridge preferably does not exceed about 1 mm.

The base 6 of the member 2 is of substantially uniform thickness except for the protrusions 11. The outer wall 8 is of substantially uniform thickness except for the ridge 12. The thickness of the inner wall 9 is substantially uniform, and the thickness of each wall corresponds substantially to the thickness of the other walls, except for the protrusions 11 and the ridge 12.

The base 6 intentionally has a width greater than that of a person's teeth. This ensures that the pattern may be used for the production of splints for persons whose bites are considerably different.

A pattern according to the invention may be formed in a number of different ways. Preferably, however, the pattern is formed by a molding process wherein a moldable material that is form-stable at room temperature, such as dental wax, is heated to a temperature at which it becomes flowable or pliable following which it is inserted in a mold and subjected to pressure to conform the material to the configuration of the mold cavity. The molded material is cooled, following which it is removed from the mold and trimmed to form the finished pattern.

One form of mold for producing the pattern is shown in FIGS. 3-4 as comprising a mandibular mold half 15 having a flask 16 filled with a stone material 17 in which is formed a protruding, arcuate die 18. Along the base of the outer surface of the die 18 is a groove 19, the purpose of which is to form a well defined free edge for the outer wall 8 of the pattern.

The mold half 15 cooperates with a maxillary mold half 20 having a flask 21 also filled with stone material 22 and in which is a cavity 23 of such size and configuration as to accommodate the die 18. The flask 21 has locating pins 24 adapted for removable accommodation in openings 25 provided in the flask 16 to enable the die 18 to be located properly within the cavity 23. The relative sizes of the die 18 and the cavity 23, of course, are such as to provide adequate space between their confronting surfaces to enable the formation therebetween of the base and side walls of the pattern. In addition, the cavity 23 has depressions 26 and 27 for the formation of the protrusions 11 and the ridge 12, respectively.

The mold disclosed in FIGS. 3-4 is a manually operable mold. In the use of such mold, the two halves are separated, following which a sheet of dental wax or other suitable moldable material is heated to a temperature at which it becomes plastic, thereby enabling it to be shaped manually to conform roughly to and overlie the die 18. While the material is still plastic, the mold half 20 is placed over the mold half 15 with the die 18 and the plastic material thereon in registration with the cavity 23. Thereafter, the mold is subjected to pressure of between about 2500 and 3000 p.s.i.

The quantity of plastic material used in the molding process is more than enough to fill completely the space between the confronting surfaces of the die 18 and the cavity 23. Accordingly, when the mold is subjected to pressure, the plastic material will be capable of flowing to all parts of the mold cavity and completely fill the latter. Sufficient space is provided between the stone material of the confronting mold halves to enable excess material to escape the cavity as flash. Following the application of pressure, the molded part is permitted to cool, after which the mold halves are separated and the rough molded part removed and trimmed to form the finished pattern.

The production of a pattern by means of the disclosed molding technique is so simple that a relatively unskilled person may make a large number of patterns per day.

The finished pattern 1 may be used by a dentist, dental assistant, or dental technician to produce an occlusal splint. As shown in FIG. 2, the first step in the procedure is to heat the pattern so that it becomes sufficiently pliable to be placed in a patient's mouth or between the maxillary and mandibular jaw models in an articulator and shaped as necessary to conform to the patient's bite. In placing the pattern in the patient's mouth or between the jaw models, the ridge 12 should be located at the midline of the jaw. This will ensure proper orientation of the pattern even though the width of the base 6 is greater than that of the patient's teeth.

If the splint to be formed is a maxillary splint, the pattern should be applied to the maxillary jaw; if the splint to be formed is a mandibular splint, the pattern should be applied to the mandibular jaw. Following application of the pattern to the patient's mouth or model, and while the material of the pattern is still formable, the maxillary and mandibular jaws are moved toward one another to obtain an occlusion. The pattern then is placed in an investment mold and invested, following which it is removed and replaced by acrylic material which is cast, cured, and then polished to form the finished splint.

The pattern 1 disclosed herein is one for the production of a maxillary splint. Accordingly, the high points of the protrusions 11 for forming the cuspid risers are substantially coplanar with the surface of the labial side wall. However, if a mandibular splint is to be formed, the cavity in the confronting mold surfaces may be reconfigured to provide in the pattern protrusions like the protrusions 11 but located substantially coplanar with the surface of the buccal wall. The cavity of the mold also will be shaped to provide a depression like the depression 27 to produce a ridge like the ridge 12 at the midpoint of the bight of the mandibular pattern.

Since the pattern illustrated in the drawings is a maxillary pattern, the inner wall 9 is higher than the outer wall 8 so as to lie closely against that part of the patient's palate adjacent the teeth and provide stability for the pattern while it is in the patient's mouth or the articulator. The pliability of the material from which the pattern is formed ensures proper fitting of the pattern to the mouth or articulator.

It will be understood that patterns like those described above need not be produced by the manual molding techniques disclosed. It is possible to form patterns using single- or multi-cavity injection or vacuum molding techniques.

The disclosed embodiments are representative of presently preferred forms of methods and apparatus according to the invention, but are intended to be illustrative rather than definitive thereof. The invention is defined in the claims.

What is claimed is:

1. A method of forming a pattern for subsequent use in the molding of a dental splint, said method comprising heating a sheet of waxy material that is form-stable at room temperature to an elevated temperature at which said material becomes plastic; introducing said material in its plastic state between a pair of movable mold halves having confronting surfaces forming respectively a substantially U-shaped die and a complementary cavity shaped to form a substantially U-shaped member having a pair of spaced apart limbs converging in a direction toward one end of said member and joined at corresponding ends to one another by an arcuate bight, said confronting surfaces also having complementary projections and depressions at spaced intervals along said bight; manually deforming said sheet of material in said mold while said material is in its plastic state to conform said material generally to the configuration of said die; applying sufficient force on the deformed material in said mold by movement of said mold halves toward one another to cause said material to flow throughout the space between said confronting surfaces and produce a trough-like, substantially U-shaped member having a base from one side of which spaced inner and outer side walls extend in the same direction, said base having an inner surface between said side walls that is substantially flat and an opposite, outer surface that is substantially flat except for protrusions caused by said material occupying said depressions, said side walls being of substantially uniform thickness; and cooling said member to room temperature to produce said pattern.

2. The method according to claim 1 including forming said protrusions in positions wherein the highest point of each such protrusion is substantially flush with the outer surface of the associated side wall.

3. The method according to claim 1 including forming said protrusions in positions wherein the highest point of each such protrusion is substantially flush with the inner surface of the associated side wall.

4. The method according to claim 1 including forming on the outer wall of said bight a ridge located at substantially the midpoint of said bight.

5. The method according to claim 4 wherein said ridge extends substantially the full height of said outer wall of said bight.

6. The method according to claim 4 wherein each of said walls is of substantially uniform thickness except for said ridge.

* * * * *